United States Patent [19]
Yamada et al.

[11] Patent Number: 5,693,223
[45] Date of Patent: Dec. 2, 1997

[54] COLUMN AND COLUMN DEVICE FOR LOW PRESSURE-HIGH SPEED LIQUID CHROMATOGRAPHY AND A METHOD FOR USING SAID COLUMN DEVICE

[75] Inventors: Saichi Yamada, Ichinomiya; Hideki Takeuchi, Handa; Kazunari Yamada, Nagoya; Tsuyoshi Majima, Tokai, all of Japan

[73] Assignee: NGK Insulators, Ltd., Japan

[21] Appl. No.: 802,420

[22] Filed: Feb. 18, 1997

Related U.S. Application Data

[63] Continuation of Ser. No. 348,254, Nov. 28, 1994, abandoned.

[30] Foreign Application Priority Data

Nov. 26, 1993 [JP] Japan ................................ 5-296886
Nov. 24, 1994 [JP] Japan ................................ 6-289944

[51] Int. Cl.$^6$ ............................................. B01D 15/08
[52] U.S. Cl. ..................... 210/198.2; 210/94; 210/656
[58] Field of Search ............................ 210/94, 198.2, 210/656, 635, 450; 96/101

[56] References Cited

U.S. PATENT DOCUMENTS

| | | | |
|---|---|---|---|
| 2,761,833 | 9/1956 | Ward | 210/94 |
| 3,463,320 | 8/1969 | Patterson | 210/94 |
| 3,732,981 | 5/1973 | Mendelsohn | 210/94 |
| 3,780,866 | 12/1973 | Ek | 210/198.2 |
| 3,966,609 | 6/1976 | Godbille | 210/198.2 |
| 4,155,846 | 5/1979 | Novak et al. | 210/31 C |
| 4,271,015 | 6/1981 | Moore | 210/94 |
| 4,309,286 | 1/1982 | Lenihan, Jr. et al. | 210/198.2 |
| 4,384,957 | 5/1983 | Crowder | 210/198.2 |
| 4,476,017 | 10/1984 | Scharff | 210/94 |
| 4,529,511 | 7/1985 | Breeden | 210/94 |
| 4,554,071 | 11/1985 | Ruijten | 210/198.2 |
| 4,557,830 | 12/1985 | Onitsuka | 210/198.2 |
| 4,675,104 | 6/1987 | Rai | 210/198.2 |
| 4,755,293 | 7/1988 | Sakamoto | 210/198.2 |
| 4,787,971 | 11/1988 | Donald | 210/198.2 |
| 4,865,728 | 9/1989 | Larsson | 210/198.2 |
| 4,888,112 | 12/1989 | Kronwald | 210/198.2 |
| 4,891,133 | 1/1990 | Colvin | 210/198.2 |
| 4,927,531 | 5/1990 | Sakamoto | 210/198.2 |
| 4,971,688 | 11/1990 | Francois | 210/94 |
| 5,037,544 | 8/1991 | Snyder | 210/198.2 |
| 5,089,125 | 2/1992 | Hart | 210/198.2 |
| 5,167,810 | 12/1992 | Vassarotti | 210/198.2 |
| 5,171,430 | 12/1992 | Beach | 210/94 |
| 5,238,556 | 8/1993 | Shirkhan | 210/198.2 |
| 5,360,544 | 11/1994 | Nakaso | 210/198.2 |
| 5,366,621 | 11/1994 | Bidell | 210/198.2 |
| 5,378,359 | 1/1995 | Huse | 210/198.2 |
| 5,395,521 | 3/1995 | Jagadeeswaran | 210/198.2 |
| 5,433,847 | 7/1995 | Rice | 210/198.2 |
| 5,462,659 | 10/1995 | Saxena | 210/198.2 |
| 5,482,628 | 1/1996 | Schick | 210/198.2 |

FOREIGN PATENT DOCUMENTS

| | | | |
|---|---|---|---|
| 0346082 | 12/1989 | European Pat. Off. | 210/198.2 |
| 2238257 | 5/1991 | United Kingdom | 210/198.2 |

OTHER PUBLICATIONS

Perfusion Chromatography An Approach to Purifying Biomolecules, Bio/Technology, vol. 8, Mar. 1990, pp. 203–206.

*Primary Examiner*—Ernest G. Therkorn
*Attorney, Agent, or Firm*—Parkhurst, Wendel & Burr, L.L.P.

[57] ABSTRACT

A column for low pressure-high speed liquid chromatography, including a column body being made of a transparent or translucent plastic and having a column chamber, said column body having one end opened and the other provided with an outflow opening, a pair of upstream and downstream filters for shutting a granular filler inside said column chamber, and a head portion being made of a plastic and detachably being fitted to said one open end of the column body and having an inflow through opening communicating with interior of said column body. A column device includes the column and a method for using the column device are also disclosed for low pressure-high speed liquid chromatography.

12 Claims, 14 Drawing Sheets

FIG_1

FIG_4
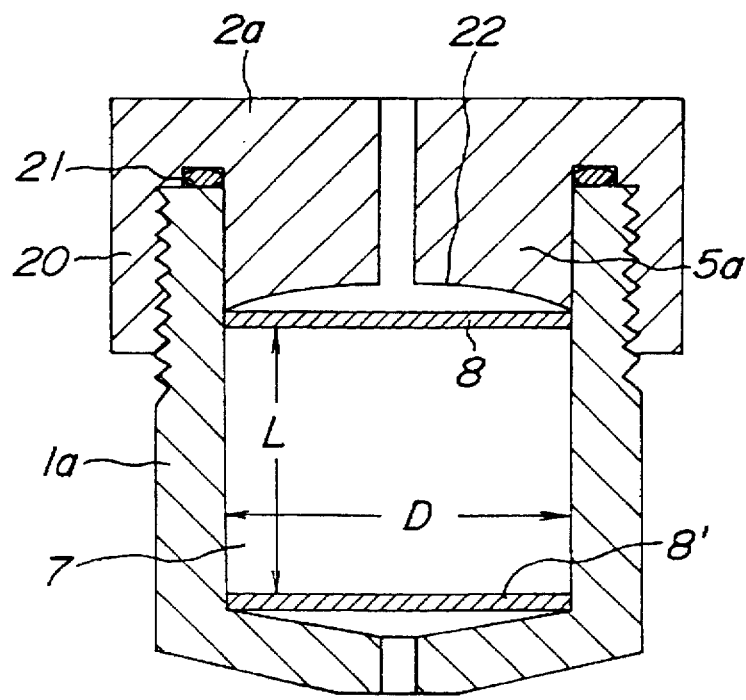
FIG_5
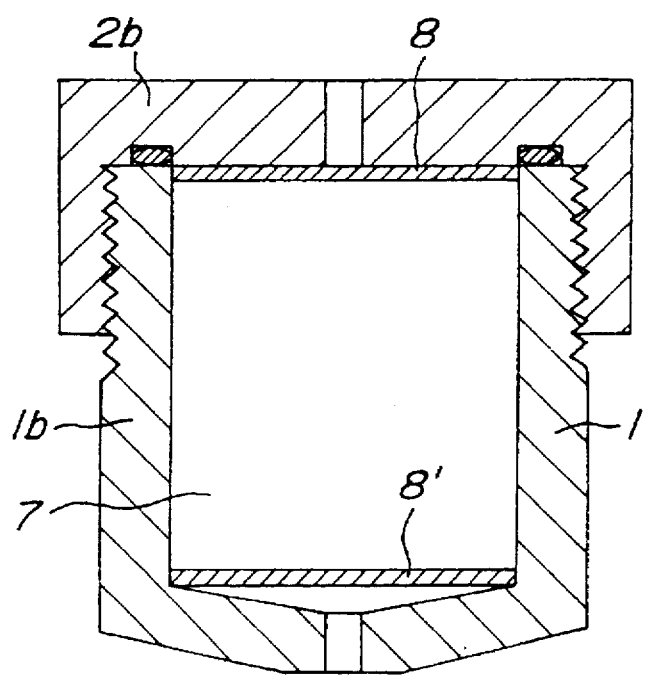

FIG_8a
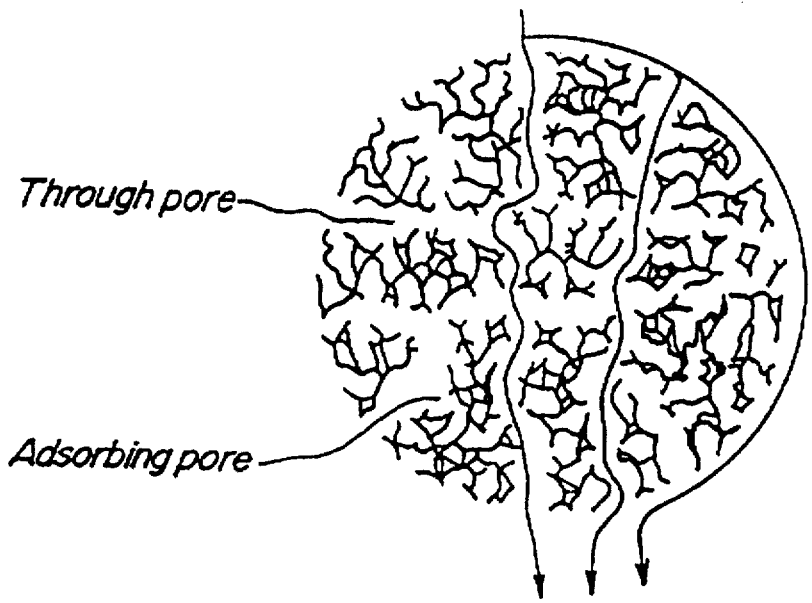
Through pore
Adsorbing pore
FIG_8b
Hyper D™
Hyper D Gel-In a shell particle structure Combines the High Capacity of a Soft Gel with the Speed of a Rigid Bead.
Rigid Hyper D™ Media
"Gel-In a Shell"
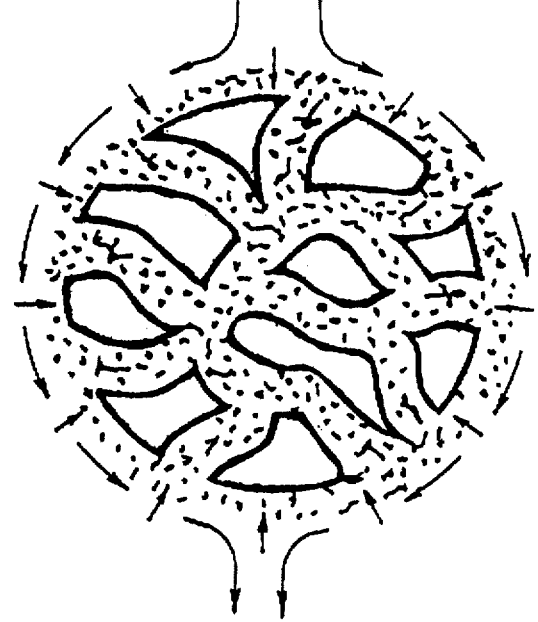
Higher Binding Capacity/Higher Flow Stability
(Rigid)

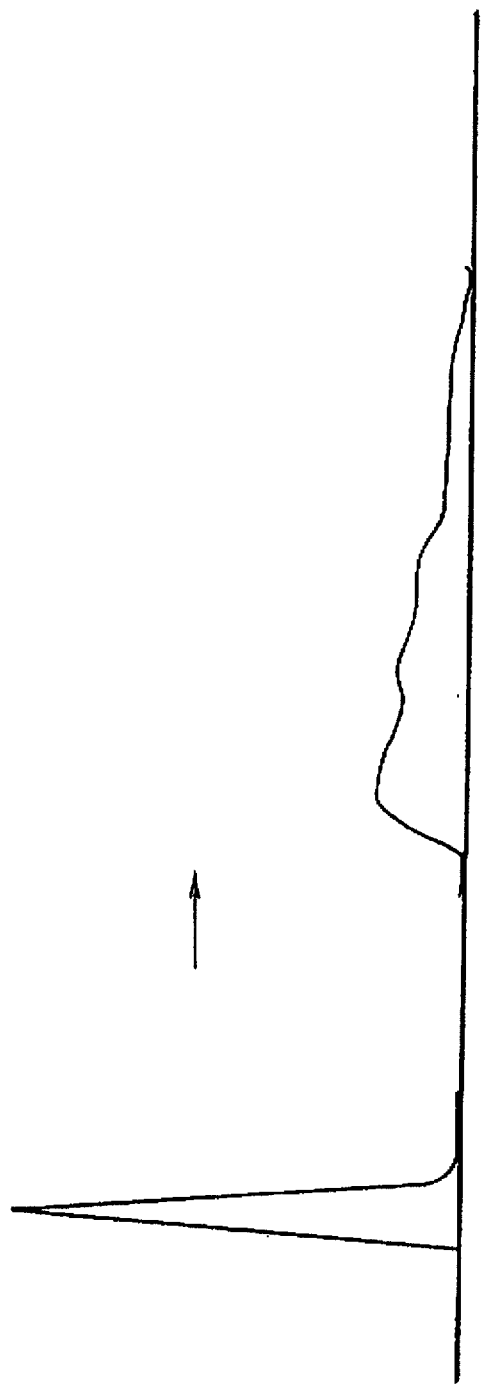
FIG_9

FIG_13

FIG_14

FIG._16

Ion exchange chromatography chart
1. Ovalbumin
2. BSA 5,693,223

1

COLUMN AND COLUMN DEVICE FOR LOW PRESSURE-HIGH SPEED LIQUID CHROMATOGRAPHY AND A METHOD FOR USING SAID COLUMN DEVICE

This is a Continuation of application Ser. No. 08/348,254 filed Nov. 28, 1994, now abandoned.

BACKGROUND OF THE INVENTION (1) Field of the Invention

The present invention relates to a column and a column device for low pressure-high speed liquid chromatography to be used for separating and purifying materials, particularly physiologically active materials such as proteins and peptides, and to a method for using said column device.

(2) Related Art Statement

Heretofore, the physiologically active materials such as proteins and peptides have been ordinarily separated and purified by low-pressure chromatography. According to this method, a soft gel is charged into a cylindrical glass column, and an intended material is separated and purified by spontaneously flowing a raw material liquid through the soft gel. However, since this method called an open system requires a long time for the separation and purification in a practical scale, investigation has been recently undertaken to make the separation and purification by using a high speed liquid chromatography (HPLC) in a shorter time.

According to recently developed and employed high speed liquid chromatography, a raw material liquid is passed through a granular filler charged into a slender stainless column having high pressure resistance for separating and purifying an intended material. However, the separation and purification with such a stainless column has the following problems. That is, (1) since even stainless steel may be corroded, the raw material liquid may be contaminated. (2) Since the stainless column is opaque, presence of a bubble in the filler or presence of the raw material liquid flowing through the filler in an normal state cannot be visually observed. Consequently, fluctuation or deterioration of measurement results cannot be preliminarily prevented from the outside. Further, even if the measurement result becomes relatively broad, it is difficult to correctly grasp a reason therefor. (3) Further, since the conventional high speed liquid chromatography is long and the grain size of the granular filler charged into the column is small, the pressure loss is large when the liquid is passed through the filler in the column device. Accordingly, in order to effect the separation and purification at a high speed, the raw material liquid must be fed into the column under high pressure. Therefore, it is necessary that sufficient pressure resistance is afforded upon the stainless column, and a high pressure pump is used. This makes the equipment very expensive. (4) When the column equipment is scaled up for effecting the separation and purification in a large amount, the weight of the column becomes greater. Thus, this makes it difficult to adopt the stainless column, also from the standpoint of the cost. (5) Furthermore, there is the possibility that protein or the like to be separated and purified is deactivated under the separation and purification at high pressure.

On the other hand, since the raw material liquid can be passed through a membrane chromatography device using a separating membrane under a relatively low pressure, no high pressure acts in such a membrane chromatography device even at a high flow rate. Therefore, since the degree of the pressure proof in the membrane chromatography device can be reduced as compared with the stainless column, the cost of the column equipment can be decreased. However, an amount of the membrane chromatography device capable of adsorbing a material is far smaller than that of the granular filler in the high speed liquid chromatography. Therefore, although the separation and purification can be effected speedily at a high flow rate, the amount of the material recovered is low.

When an inorganic glass column is used for separating a liquid blood-origin medicine from a raw liquid to be treated, silanol groups in the glass deactivate protein in the blood-origin medicine.

SUMMARY OF THE INVENTION

The present invention is to provide a column and a column device for low pressure-high speed liquid chromatography to be used for separating and purifying materials, particularly physiologically active materials such as proteins and peptides, and to a method for using said column device, the column, the column device and the method having been accomplished to solve the problems possessed by the above mentioned prior art and being free from the contamination of the raw material liquid with rust, etc., and allowing the presence of bubbles in the filler (carrier) and the passing state of the raw material liquid through the column to be visually observed during the separation and purification. The column and the column device are light in weight and easy to install.

The column for low pressure-high speed liquid chromatography according to the present invention, which column has been accomplished to solve the above problems, comprises a column body being made of a transparent or translucent resin and having a column chamber therein, said column body having one end opened and the other provided with an outflow opening, a pair of upstream and downstream filters for shutting a granular filler inside said column chamber, and head portion being made of a resin and detachably being fitted to said one open end portion of the column body and having an inflow through opening communicating with the interior and the exterior of said column body.

The following embodiments are considered preferable as the column for low pressure-high speed liquid chromatography according to the present invention (1) The head portion is a transparent or translucent resin, and each of said column body and each of said head portion is made of one material selected from the group consisting of polypropylene, high density polyethylene, polysulfone and polyvinyl chloride.

(2) A stepped portion is circumferentially provided at each of sealingly contacting surfaces of said column body and said head portion, and said stepped portion of the column body engages with that of head portion.

(3) The head portion comprises a large diameter portion and an inserting portion extendingly axially from said large diameter portion, said inserting portion is sealingly fitted into an open end portion of the column body.

(4) The inserting portion of the head portion has a cylindrical shape, a threaded portion is provided at an outer peripheral surface of the inserting portion, a corresponding threaded portion is provided at an inner peripheral surface of the open end portion of the column body, said inner peripheral surface of the open end portion being made cylindrical, and said thread portions mesh with each other.

(5) The head portion has a cap-shaped form, a threaded portion is provided at a cylindrical inner peripheral portion of an outer peripheral portion of the cap-shaped head portion, a corresponding threaded portion is provided at an outer peripheral portion of the open end portion of the column body, said outer peripheral portion of the open end portion being made cylindrical, said threaded portions mesh with each other.

(6) A circumferential groove is provided at a surface of the head portion facing an end face of the open end portion of the cylindrical column body, and an O-ring is fitted into said circumferential groove for sealing between the end face of the open end portion of the column body and the opposed surface of the head portion.

(7) A surface of said head portion facing an interior of the cylindrical column body is shaped in a conical form tapered in an axially outward direction.

(8) A pressure-proof ring is fitted around an outer periphery of the open end portion of the column body to which the head portion is fitted.

(9) The column chamber has a cylindrical shape, and a ratio of an axial length to/a diameter of the column chamber is not more than 2.

(10) The column is constituted by the column body having a cylindrical outer peripheral surface and a cylindrical inner peripheral surface forming the column chamber.

The column device for low pressure-high speed liquid chromatography according to the present invention comprises any of the above columns and a granular filler charged into said column chamber.

Further, the method for separating and purifying a physiologically active material according to the present invention is characterized by using the above column device for low pressure-high speed liquid chromatography at a high speed from 50 column volume/hr to 200 column volume/hr under a high pressure from 0.2 kgf/cm$^2$ to 7 kgf/cm$^2$.

The raw material liquid is passed through the column device for low pressure-high pressure liquid chromatography in the same way as in ordinary column devices, so that a material such as protein in the raw material liquid is absorbed onto the granular filler charged into the column chamber. The column, the column device and the column device-using method exhibit the following effects.

(1) Since the column body and the head portion of the column for the low pressure-high speed liquid chromatography are made of plastic, the raw material liquid to be treated is not contaminated with rust or the like.

(2) Since at least the column body is made of the transparent or translucent resin, presence of a bubble mixed into the granular filler charged into the column chamber of the column body can be easily determined from the outside. Therefore, even if bubbles are contained in the filler, the bubbles can be easily removed by attaching a pouring syringe to the inflow opening of the column head portion or the outflow opening of the column body and pouring a solvent sucked in the syringe into the column body under pressure. Accordingly, the intended material can be excellently separated and purified. Furthermore, when the head portion is also made of the transparent or translucent resin, contamination of the filler with such bubbles can be more effectively discovered.

(3) Since the column and the head portion are made of the resin, the column and column device are light in weight and easy to handle, so that the column device for the low pressure-high speed liquid chromatography can be easily fitted to a separating/purifying system.

(4) Since the column body and the head portion are made of the resin, the column and the column device can be less expensively produced.

(5) When the surface of the head portion facing an interior of the column body is shaped in a conical form tapered in an axially outward direction, bubbles which happen to mix into the filler, can be easily discharged out of the column.

(6) When the pressure-proof ring is press fitted around the outer periphery of a portion of the column body to which the head portion is fitted, the pressure ring prevents the column body from radially outwardly expanding due the internal pressure acting in the column chamber. Accordingly, the breakage of the column and the leakage of the liquid can be effectively prevented.

(7) When the column chamber has a cylindrical shape and the ratio of axial length to the diameter of the column chamber is set at not more than 2, the physiologically active material such as protein can be effectively separated and purified at a high speed under low pressure.

(8) When the column is constituted by the column body being a cylindrical outer peripheral surface and a cylindrical inner peripheral surface forming the column chamber, the productivity of the column can be enhanced.

These and other objects, features and advantages of the invention will be appreciated upon reading the following description of the invention when taken in conjunction with the attached drawings, with the understanding that some modification, change and variation of the same could be made by those skilled in the art to which the invention pertains without departing from the spirit of the invention or the scope of claims appended hereto.

BRIEF DESCRIPTION OF THE DRAWINGS

For a better understanding of the invention, reference is made to the attached drawings, wherein:

FIGS. 4 through 7 are sectional views of further embodiments of the column for low pressure-high speed liquid chromatography according to the present invention in an assembled state, respectively;

FIG. 8a is a figure schematically illustrating a flowing state of a raw material liquid through a grain of a filler;

FIG. 8b is a figure schematically illustrating a flowing state of a raw material through a grain of Hyper D™ gel;

FIG. 9 is a figure schematically illustrating an influence of a bubble or bubbles upon a separation result when an affinity chromatography carrier is used;

DETAILED DESCRIPTION OF THE INVENTION

Figure 1:
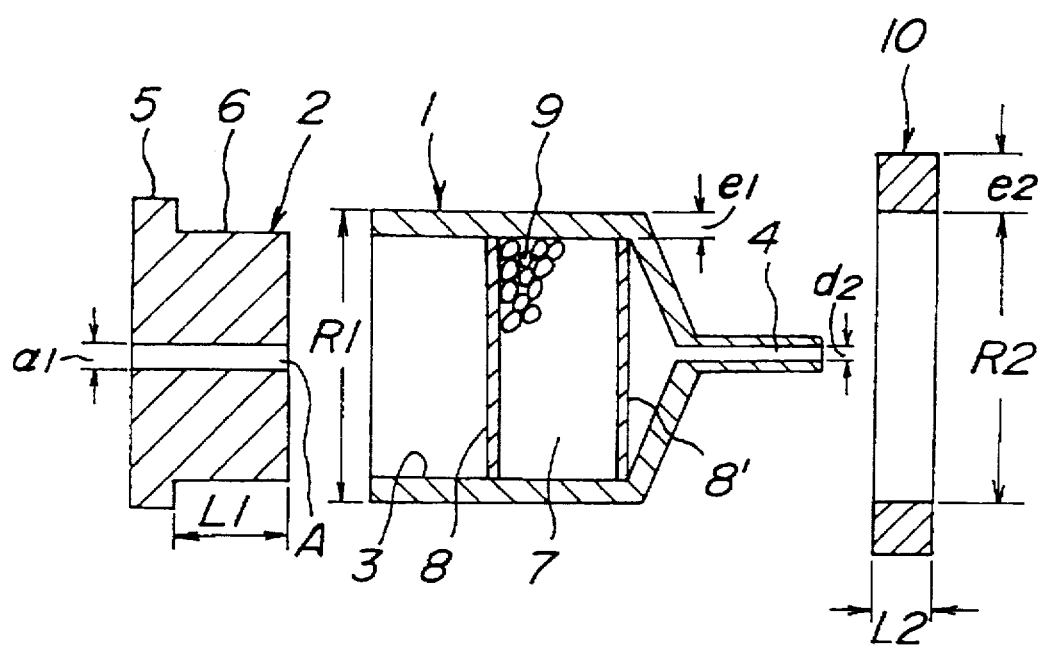
FIG. 1 is a sectional view of an embodiment of the column for low pressure-high speed liquid chromatography according to the present invention in a disassembled state.

As the transparent or translucent resins to be used for the cylindrical column body and the head portion of the column according to the present invention, for example, mention may be made of polypropylene, high density polyethylene, polysulfone and polyvinyl chloride. Among them, polypropylene is considered preferred. The thickness of the column body and that of the head may be appropriately determined in view of the separating and purifying pressure and the kind of the materials used, etc. The term "resin" used herein includes "plastics".

In order to visually observe the existence of a bubbles having the diameter of not less than 1 mm from the outside of the column device, the linear light transmittance of the column is required to be not less than 8%. In the case of translucent polypropylene resin, it is necessary that the linear light transmittance is 2% or more and the thickness is not more than 6 mm so that the flowing of the liquid through the column device may be visually observed from the outside, whereas the linear light transmittance is not less than 8% or more so that the bubble having the diameter of 1 mm or more may be visually observed from the outside of the column. In that case, the thickness of the resin is not more than 3 mm.

A column chamber is formed inside the cylindrical column body. The shape of the column chamber is generally designed to be cylindrical. However, so long as the liquid is assuredly passed through the column chamber uniformly, the column chamber is not necessarily limited to the cylindrical shape. Further, in order to smoothly flow the raw material liquid through the column and facilitate removal of any bubbles, the internal shape of the column body on the side of the outflow opening is preferably designed in a conical shape having the outflow opening as a vertex.

The fitting configuration and the dimensions of the cylindrical column body and the head portion are appropriately determined in view of the separating and purifying pressure. For example, when the head portion includes a large diameter portion and an inserting portion extending axially from the large diameter portion and the inserting portion is sealingly fitted into of the open end portion of the column body, the outer diameter of the outer peripheral portion of the inserting portion is slightly set greater than the inner diameter of the inner peripheral surface of the open end portion of the column body. The outer diameter of the outer peripheral portion of the inserting portion and the inserted (press-fitted length) of the inserting portion in the open end portion are so set that when the inserting portion is fitted into the open end portion of the column body, the inserting portion holds its position in the open end portion against a given internal pressure.

A pair of upstream and downstream filters are made of a porous resinous material such as Teflon, and have such an outer diameter as slightly greater than the inner diameter of the column chamber. The filters are fixedly press fitted inside the column chamber.

The filler is charged into the column chamber between the upstream and downstream filters inside of the column for the low pressure-high speed liquid chromatography according to the present invention. As such fillers, for example, mention may be made of various chromatography carriers such as an ion exchange chromatography carrier, a hydrophobic chromatography carrier, reverse phase chromatography carrier and affinity chromatography carrier. When the separation and purification is effected at a high flow rate, the high speed affinity chromatography carrier using a porous polymer or silica as a material and having high hardness and a high adsorbing capacity is used. This carrier enables the separation even at a high flow rate of 50–200 column volume/hr at a high yield without any substantial loss, and exhibits an adsorbing power of not less than 10 mg-IgG/ml (gel) in the case of an antibody (mouse IgG at 10% breakthrough). However, if the flow rate is more than 200 column volume/hr, this power largely decreases. The grain diameter of the carrier used in the present invention is preferably 20–50 μm from the standpoint that the raw material liquid should be passed through the carrier at a high speed with no greater pressure loss.

As the filler, a material made of a crosslinked copolymer of stylene and divinylbenzene and composed of grains having relatively large or thick holes (through pores) and numerous small or thin pores (adsorbing pores) branched from the large or thick pores may be used (See FIG. 8a). As such a material, for example, a filler commercially available under a tradename of Poros™ gel manufactured by PerSeptive Biosystems (U.S.A.) may be used. This Poros™ gel may be used as a gel for Perfusion Chromatography. Further, as the above filler, a composite structural material may be used, in which a hydrogel having adsorbing groups is filled in a lattice made of polystyrene. As such a material, a filler having a rigid composition matrix and commercially available under a tradename of Hyper D™ gel manufactured by Biosepra Inc. (U.S.A.) may be used. Hyper D™ gel may be used as a gel for Hyperdiffusion Chromatography. In the following table, Poros ™ and Hyper D™ are given by way of example.

POROS® media are based on a highly crosslinked polystyrene/divinylbenzene support matrix which provides high mechanical strength and excellent resistance to a broad range of solvents and chemicals, including pH 1–14. To create a biocompatible environment for delicate biological molecules, this base is then coated with a crosslinked polymer creating a uniform charge-neutral surface with high concentrations of hydroxylgroups. This hydrophilic surface coating is also highly chemically resistant and functions as a reliable platform for derivitization with a wide range of functional groups.

The resulting chromatographic particle has full mechanical and chemical resistance, performs without non-specific adsorption, is non-denaturing to proteins and provides for enhanced recovery of biological activity.

TABLE 1

Comparison of Protein A gels

| Filler (particle diameter) | Carrier base | Human IgG adsorbing capacity at 10% breakage [mg/ml – gel] | alkali resistance (durability) |
|---|---|---|---|
| Hyper D Protein A (35 μm) | rigid, polystyrene composite | 19–20 | ☉ |
| Poros 20 Protein A (20 μm) | Crosslinked polystyrene/divinylbenzene | 19–20 | o |
| Poros 50 Protein A (50 μm) | | 10–11 | |
| Sepharose F.F. Protein A (45–165 μm) | Highly crosslinked agarose | 9–10 | Δ |

Measurement condition:
Flow rate . . . 60 cm/hr,
IgG conc. . . . 1 mg/ml

As the adsorbing solvent and washing solvent used in the present invention, for example, a buffer solution having a high content of a salt having a great concentration of sodium chloride, sodium sulfate or the like may be used. For example, the antibodies have been recently being fractioned in the industrial scale as diagnosis medicines. When a antibody: Mouse IgGl is to be separated with an affinity chromatography carrier using Protein A as a ligand, a high viscosity solvent (1.5M glycine+3M-NaCl, pH 8.9) is used as an adsorbing buffer solution. As to the eluting solvent, the intended material is eluted with a buffer solution having a high concentration of a salt in many cases. In these cases, the buffer solution having a high concentration of the salt is also used as the eluting solution in the case of the ion exchange chromatography and the affinity chromatography.

A variety of materials may be separated and purified by using the column for the low pressure-high speed liquid chromatography according to the present invention. As materials to be favorably separated and purified, for example, mention may be made of various proteins such as blood-coagulating factors, recombined proteins, antibody proteins and sugar proteins.

(Embodiments)

The present invention will be explained in more detail with reference to embodiments illustrated in the attached drawings.

Figure 2:
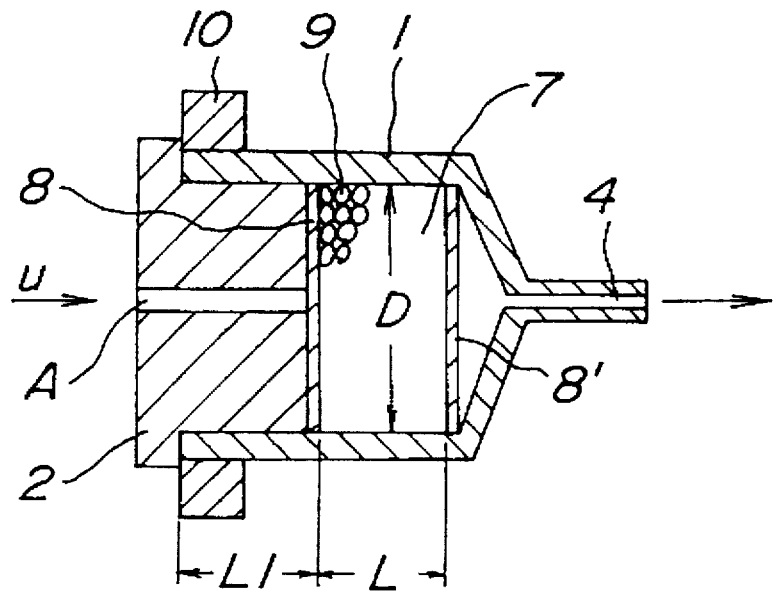
FIG. 2 is a sectional view of the embodiment of the column for low pressure-high speed liquid chromatography according to the present invention in FIG. 1 in an assembled state.

FIGS. 1 and 2 are sectional views of an embodiment of the column device for low pressure-high speed liquid chromatography according to the present invention. Into a cylindrical column body 1 made of a transparent or translucent resin is inserted a part of a cylindrical head portion 2 also made of a transparent or translucent resin at an open end portion 3 of the column body 1. The cylindrical column body 1 has a shape similar to that of a tip portion of an injector and has a thickness, "el", of 0.5 mm or more. One end of the column body is opened at 3, and the other is throttled in a funnel-shaped form with a thin outflow opening 4. The head portion 2 includes a large diameter portion 5 and an inserting portion 6 extending axially from a central portion of the large diameter portion 5. The inserting portion 3 has an outer diameter almost equal to but slightly larger than the inner diameter of the open end portion 6 of the cylindrical column body 1. As shown in FIG. 2, the inserting portion 6 is intimately and sealingly inserted into the open end portion 3 of the cylindrical column body 1. A central portion of the head portion 2 is provided with a through hole A communicating with the exterior and the interior of the column body 1. The inserting portion 6 of the head portion 2 closely engages with the inner peripheral surface of the cylindrical column body 1 over its entire outer peripheral surface so that a wide contact interface may be assured between them. The under surface of the large diameter portion 5 contacts the end face of the open end portion 3 of the column body 1. As shown in FIG. 2, the head portion 2 is inserted into the cylindrical column body 1 to define a column chamber 7 inside the cylindrical column body 1. A pair of filters 8, 8' are fitted at opposite ends of the column chamber 7, and a granular filler 9 for low pressure-high speed liquid chromatography is charged between a pair of the filters 8, 8'.

After the head portion 2 is fitted into the cylindrical column body 1, a pressure-proof ring 10 is press fitted around a portion of the outer periphery of the column body 1 into which the inserting portion 6 of the head portion 2 is fitted. The outer diameter of the large diameter portion 5 of the head portion 2 is made greater than that R1 of the column body 1, so that the ring 10 is stably held around the column body 1, while the ring is butted against the under face of the large diameter portion 5 extending radially outwardly from the column body 1. The pressure-proof ring 10 prevents the cylindrical column body 1 from expanding due to the internal pressure acting inside the column body 1. The inner diameter R2 of the pressure-proof ring 10 is made slightly smaller than the outer diameter R1 of the cylindrical column body 1. Although depending upon the materials used, leakage of the liquid from the column can be effectively prevented when the difference of R1–R2 is set at for example 0.4 mm to 0.6 mm. The pressure-proof ring 10 reinforces the cylindrical column body 1 and the head portion 2 so that the column may withstand a given internal pressure. The inserting portion 6 closely contacts the inner peripheral portion of the cylindrical column body 1 over the entire width of the outer peripheral surface to ensure the large contact area. For example, in order to afford up to 7 kg/cm$^2$ of pressure resistance between the column body 1 and inserting portion 6, the length L1 of the inserting portion 6 is set at 4 mm or more. The length of the inserting portion 6 may be appropriately determined in view of a desired internal pressure.

Each of the cylindrical column body 1 and the head portion 2 is made of a material having great strength and great hardness, being strong against an acid and alkali to be used in the chromatography, heat resistive against temperatures for the sterilization in the autoclave, and so transparent or translucent as to allow visual observation of the interior of the column from the outside. The material must not react with the liquid to be treated. For example, when a physiological material such as protein is to be separated and purified, the materials for the column body and the head portion must be materials not reacting with the physiological material.

As the resins satisfying the above requirements, for example, thermoplastic resin such as polypropylene, high density polyethylene, polysulfone and/or polyvinyl chloride may be preferably used. In this embodiment, the cylindrical column body 1 and the head portion 2 are made of polypropylene. On the other had, the material of the pressure-proof ring 10 is not limited to any one. When the pressure-proof ring 10 is made of a resin, the resin needs to have strength and hardness. From the above point of view, polyvinyl chloride is used as the pressure-proof ring 10 in this embodiment. When the pressure-proof ring 10 is made of polyvinyl chloride, the width L2 and the thickness e2 of the pressure-proof ring 10 are set at 3 mm or more and 3 mm or more, respectively. The filters 8, 8' are made of a porous material such as Teflon resistant to adsorption of protein or the like, having a number of pores allowing passage of the liquid and the solution but not allowing the passage of the granular filler therethrough. As the granular filler 9, a variety of chromatography carriers such as an ion exchange chromatography carrier, a hydrophobic chromatography carrier, a reverse phase chromatography carrier and an affinity chromatography carrier may be used. In order to effect the separation and purification at high flow rate, a hard gel made of a material such as a porous polymer or silica is used. The carrier preferably has the grain size of 20 µm to 50 µm from the standpoint of allowing the passage with a low pressure loss at high flow rate.

In this embodiment, the column chamber 7 is designed in a low-aspect shape having a ratio of an axial length L/a diameter D being 2 or less. By so constructing, the pressure loss can be suppressed to a low level even when the liquid is flown through the column at a high flow rate. Therefore, no high pressure need not be applied for flow of the liquid through the column. Consequently, the breakage of the cylindrical column body 1 and the head portion 2 made of the resin(s) as well as the leakage of the liquid can be prevented.

Figure 3:
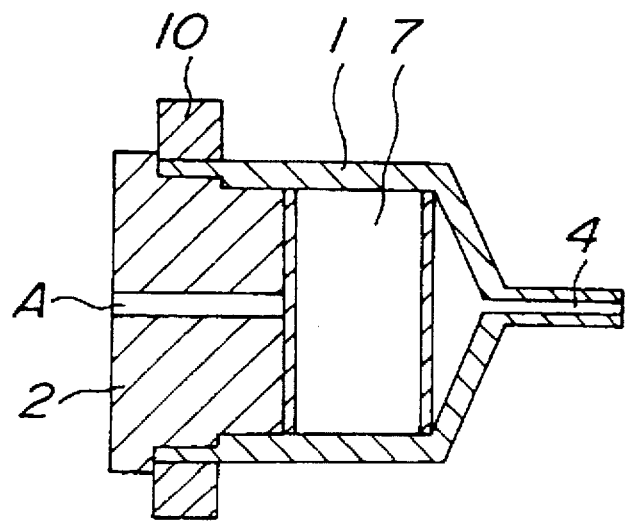
FIG. 3 is a sectional view of another embodiment of the column for low pressure-high speed liquid chromatography according to the present invention in an assembled state.

FIG. 3 shows another embodiment of the low pressure-high speed liquid chromatography according to the present invention, which embodiment is the same as that illustrated in FIGS. 1 and 2 except for the configurations of the column body and the head portion. In the column device shown in FIG. 3, a stepped portion is provided at each of corresponding contact outer and inner peripheral surfaces of the column body 1 and the head portion 2, respectively, and the stepped portions mesh with each other to effectively prevent the leakage of the liquid through the contacting interface between the column body 1 and the head portion 2.

Figure 6:
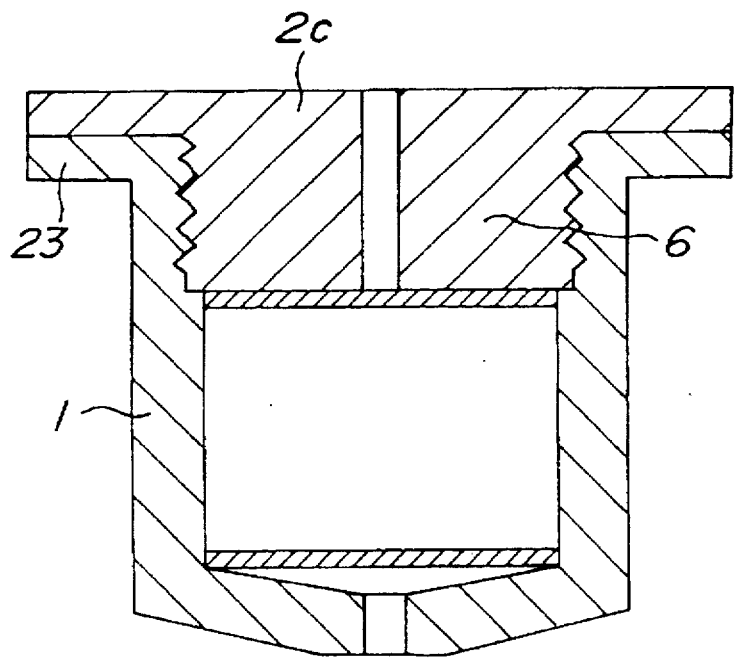
Figure 7:
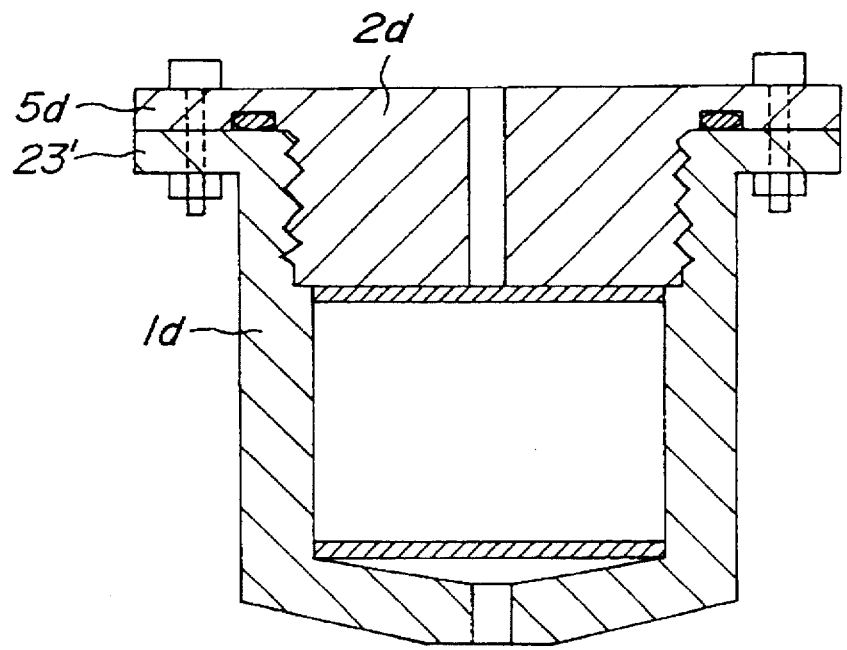

FIGS. 4 through 7 illustrate further embodiments of the low pressure-high speed liquid chromatography according to the present invention. In FIG. 4, an annular projection 20 is provided at an outer peripheral portion of a large diameter portion of a head 2a, and an inner peripheral surface of the projection 20 and a corresponding outer peripheral surface of a column body 1a are threaded, and these threaded portions mesh with each other. An O-ring 21 is provided in an annular groove at the head portion to ensure liquid tightness. In this embodiment, a portion of the surface of the inserting portion of the head facing the interior of the cylindrical column body 1a is designed in an axially inwardly conical shape 22 so as to facilitate removal of bubbles. The embodiment of FIG. 5 is substantially the same as that in FIG. 4 except that the inserting portion 5a in FIG. 4 is omitted. In the embodiment of FIG. 6, the contacting inner peripheral surface of the column body 1c and the contacting outer peripheral surface of the inserting portion 6c of the head portion 2c are threaded, and the head portion is tightened to the column body by meshing these threaded portions with each other. An annular projection 23 is extended radially outwardly from the open end portion of the column body along the large diameter portion of the head portion. When the inserting portion of the head portion is screwed into the open end portion of the column body, the under face of the large diameter portion of the head portion is closely fitted to the upper face of the annular projecting 23 of the column body to ensure liquid tightness. In this embodiment, no O-ring is provided unlike the embodiments in FIGS. 4 and 5, such an O-ring may be provided to enhance the liquid tightness. The embodiment of FIG. 7 differs from that in FIG. 6 in that an O-ring is provided and the large diameter portion 5d of the head portion 2d and the annular projection 23' of the column body are tightened by bolts and rings to further enhance the liquid tightness.

FIG. 8a is a figure for schematically illustrating the state that the raw material liquid flows through a grain of the filler. The raw material liquid flows through-pores formed in the filler grain, and an intended component in the raw material liquid is adsorbed in adsorbing pores.

Figure 10:
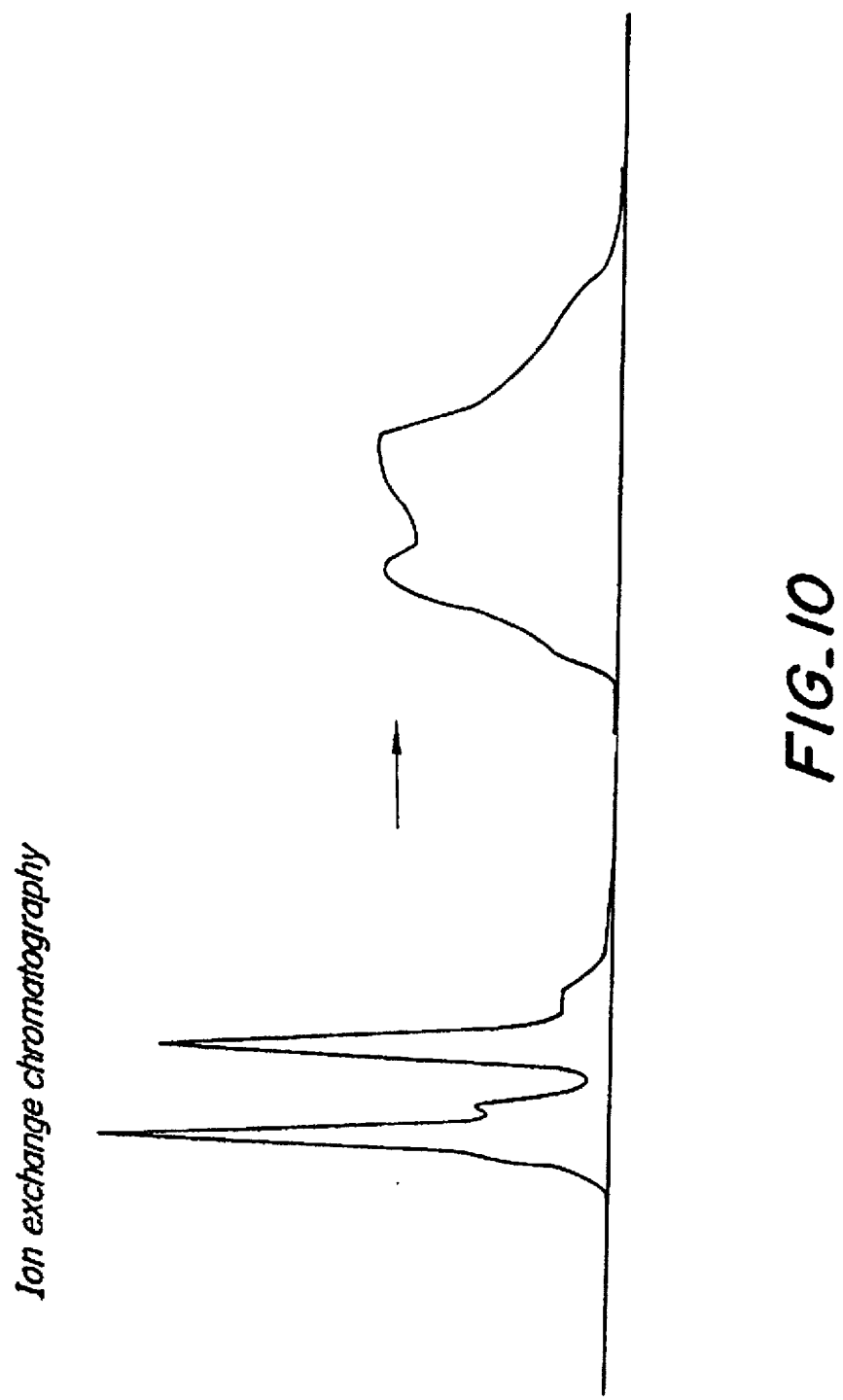
FIG. 10 is a figure schematically illustrating an influence of a bubble or bubbles upon a separation result when an ion exchange chromatography carrier is used.

FIGS. 9 and 10 are figures for illustrating effects of a bubble or bubbles upon separation results when an affinity chromatography carrier and an ion exchange chromatography carrier are used, respectively. In each of these figures, the left side measurement chart gives a separation result in a normal state, whereas the right side one is a chart of a measurement result which is collapsed and broad. In the column device for the low pressure-high speed liquid chromatography according to the present invention, any bubble present in the column device can be visually observed from the outside. Accordingly, the bubble can be visually easily removed, and the separation and purification operation can be effected in the normal state.

Figure 11:
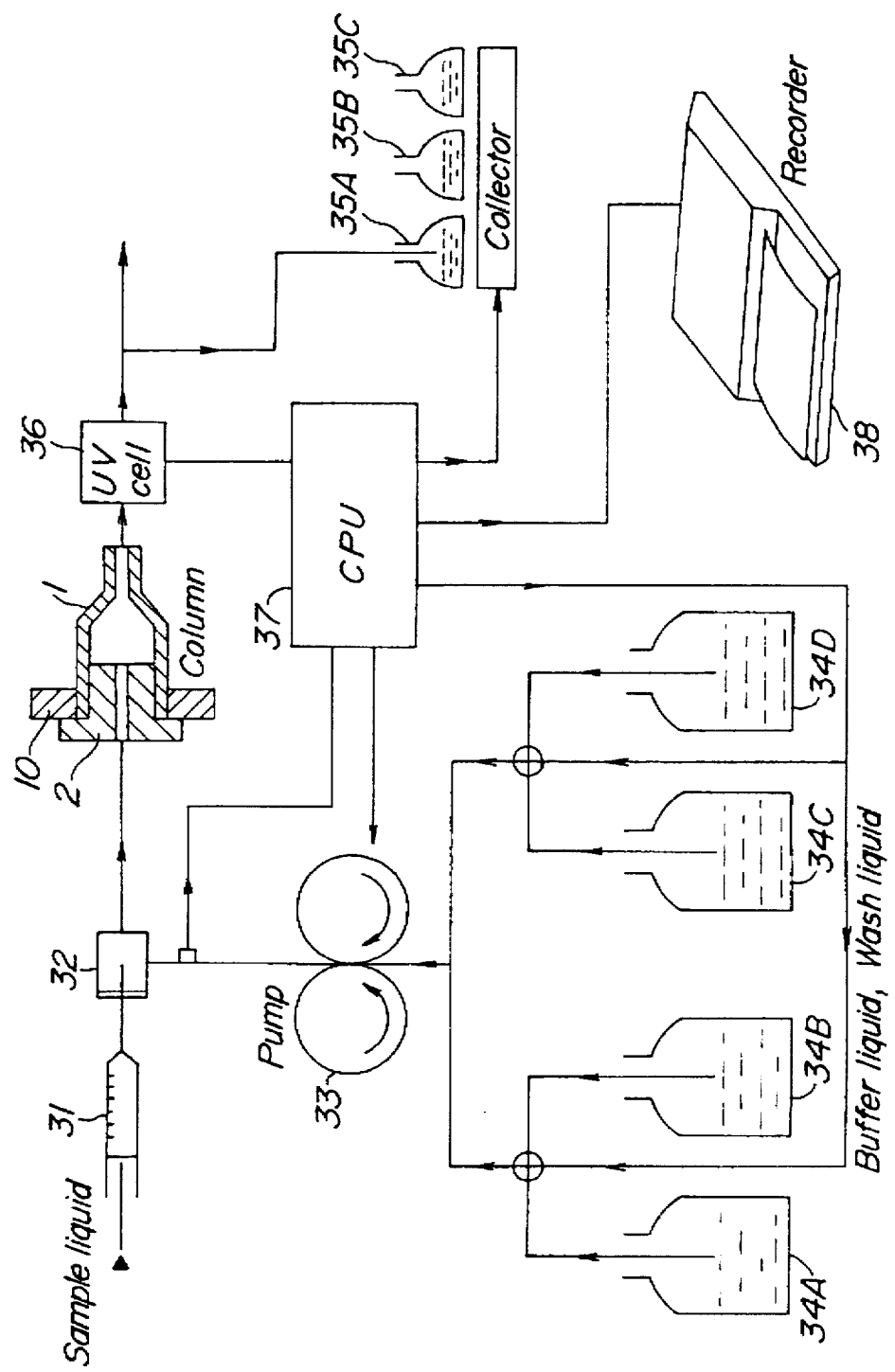
FIG. 11 is a figure schematically illustrating a separating/purifying system using the column device for low pressure-high speed chromatography as shown in FIGS. 1 and 2.

FIG. 11 shows an example of a separating/purifying system using a column device for the low pressure-high speed liquid chromatography according to the present invention (Low pressure-high speed liquid chromatography system manufactured by Millipore Inc. under the name of Consep LC100). A sample liquid in a syringe 31 is fed into a mixing vessel 32, and a buffer liquid or a wash liquid in a bottle 34A, 34B, 34C, 34D is fed into the mixing vessel 32. In the mixing vessel 32, the buffer liquid is mixed in the sample liquid. The resulting mixed liquid is fed into the column device, and a material to be separated is adsorbed onto the filler. The intended material is separated, purified and collected in a collector bottle 35A, 35B, 35C, . . . by switching feeding of the buffer liquid and the wash liquid. 36 is a UV cell, and a CPU 37 controls operation of the pump, feeding of the buffer liquid, operation of the UV cell and switching of the collector bottle according to a given program. A recorder 38 displays and records results measured by the UV cell 36. In the separating/purifying system, the column device for the low pressure-high speed liquid chromatography according to the present invention is attached in a lateral direction, but the column device can be attached in a vertical direction, in an oblique direction or in an inversed vertical direction.

Conventionally, a pump (limit pressure loss: 3 kgf/cm$^2$) in which a peristaltic tube is squeezed to feed a buffer liquid or wash liquid, is used to separate and purify a useful protein such as an antibody at a low flow rate under a low pressure. The reason why the low pressure and low flow rate are employed, is that since the conventionally used carrier is a soft gel, the gel is compacted when the liquid is passed through the column device at a high flow rate. Consequently, the liquid cannot flow through the column device, and the adsorbing capacity of the carrier decreases under the high speed flow rate. Furthermore, when the physiological material such as protein is separated and purified under high pressure, the high-dimensional structure of the protein is broken to reduce the activity of the protein. Thus, the separating operation under lower pressure is desired. On the other hand, the protein has been separated and purified under the high pressure-high flow condition in the conventional column device for the low pressure-high speed liquid chromatography by using the high pressure pump and the stainless column having excellent pressure resistance. However, as mentioned above, if the physiological material such as protein is to be separated and purified under high pressure, the high-dimensional structure of the protein may be broken to deteriorate the activity of the protein. Thus, separation and purification under lower pressure is desired.

Having noted the drawbacks possessed by the conventional column device for the high speed liquid chromatography, the present invention makes it possible to separate and purify the physiological material such as protein at a high flow rate under a high pressure. For this purpose, a gear pump or a roller pump (feed rate: 3 liters/min.) is used as a pump. For example, the flow rate of a gear pump used in the low pressure-high speed liquid chromatography system Consep LC100 (Millipore Inc.) is to be controlled based on the pressure. In this pump, a high flow rate up to 50 ml/min is attainable, and its limit pressure loss is set at 7 kgf/cm$^2$ from the standpoint of the flow rate. In order to separate and purify the protein, the pressure is preferably set at not more than 7 kgf/cm$^2$. On the other hand, the flow rate is set from the standpoint of the practical separating and purifying operation, and the configuration of the column is required to satisfy the low pressure and practical flow rate. The present inventors have investigated the relationship between the pressure loss and the flow rate, and discovered that the pressure loss can be set not more than 7 kgf/cm$^2$ and the excellent separation and purification can be effected at a high flow rate of 200 column volume/hr, when the column chamber has a flat (low aspect) shape with a ratio of a length/a diameter being not more than 2. In order that the high speed type chromatography carrier may exhibit an adsorbing capacity equal to or more than that of the conventional soft gel, the column chamber has the length of not less than 5 mm when the flow rate is 200 column volume/hr. As such a high speed type chromatography carrier, a high speed type Poros® gel (crosslinked copolymer of polystyrene and divinylbenzene, manufactured by PerSeptive Biosystems) may be used.

It was experimentally made clear that the pressure loss is expressed by the following equation. The below equation is considered to be very widely applicable when the grains are charged into the column. This experimental equation was determined based on the experimental data of the pressure loss of the column when a solvent having a high viscosity (1.5M glycine+3M-NaCl, pH 8.9) was passed through the column device. As the carrier material, use may be made of the crosslinked copolymer of polystyrene and divinylbenzene (Poros® 20A, average particle diameter of 20 μm. "20", and "A" of Poros® 20A mean "Protein A" and "average particle diameter of 20 μm", respectively. Poros® 20A is an affinity chromatography carrier (average particle diameter of 20 μm) using Protein A as a ligand. The above solvent is usually used as a buffer liquid for adsorption when an antibody such as Mouse IgG1 is to be separated and purified with an affinity chromatography employing Protein A as a ligand.

$$P = A \times U \times L \times \mu$$

wherein

P: Pressure loss of column device (kgf/cm$^2$)

U: Flow rate of empty column (cm/hr)

L: Length of column chamber (cm)

μ: Viscosity (cSt)

The viscosity of the solvent is constant, and therefore P=A'×U×L. When the liquid is passed through the column device at B column volume/hr, the above equation is P=A'×B×L$^2$ (U=B×L). In order to suppress the pressure loss to not more than a given pressure Po, L$^2$≤A'×B. Therefore, the length of the column chamber can be determined case by case so that the pressure loss and the liquid-passing rate may be realized as desired. The unit "column volume/hr" means that the liquid flows in an amount equal to the volume of the column chamber per hour.

The present inventors collected experimental data by using a column device with a column chamber (volume 10 ml, inner diameter of 26 mm, a length of 18.8 mm, a tolerable limit pressure of 40 kgf/cm$^2$) by passing the solvent (1.5M glycine+3M-NaCl, pH 8.9) through the column device, and determined A'=0.0025. That is, L2≤Po/0.0025×B. Now, when the pressure loss (limit pressure of the gear pump) and the flow rate suitable for the practical separation and purification of the physiological material such as protein are set at not more than 7 kgf/cm$^2$ and 200 column volume/hr, respectively, L$^2$≤14, that is, L ≤3.74 cm.

Figure 12:
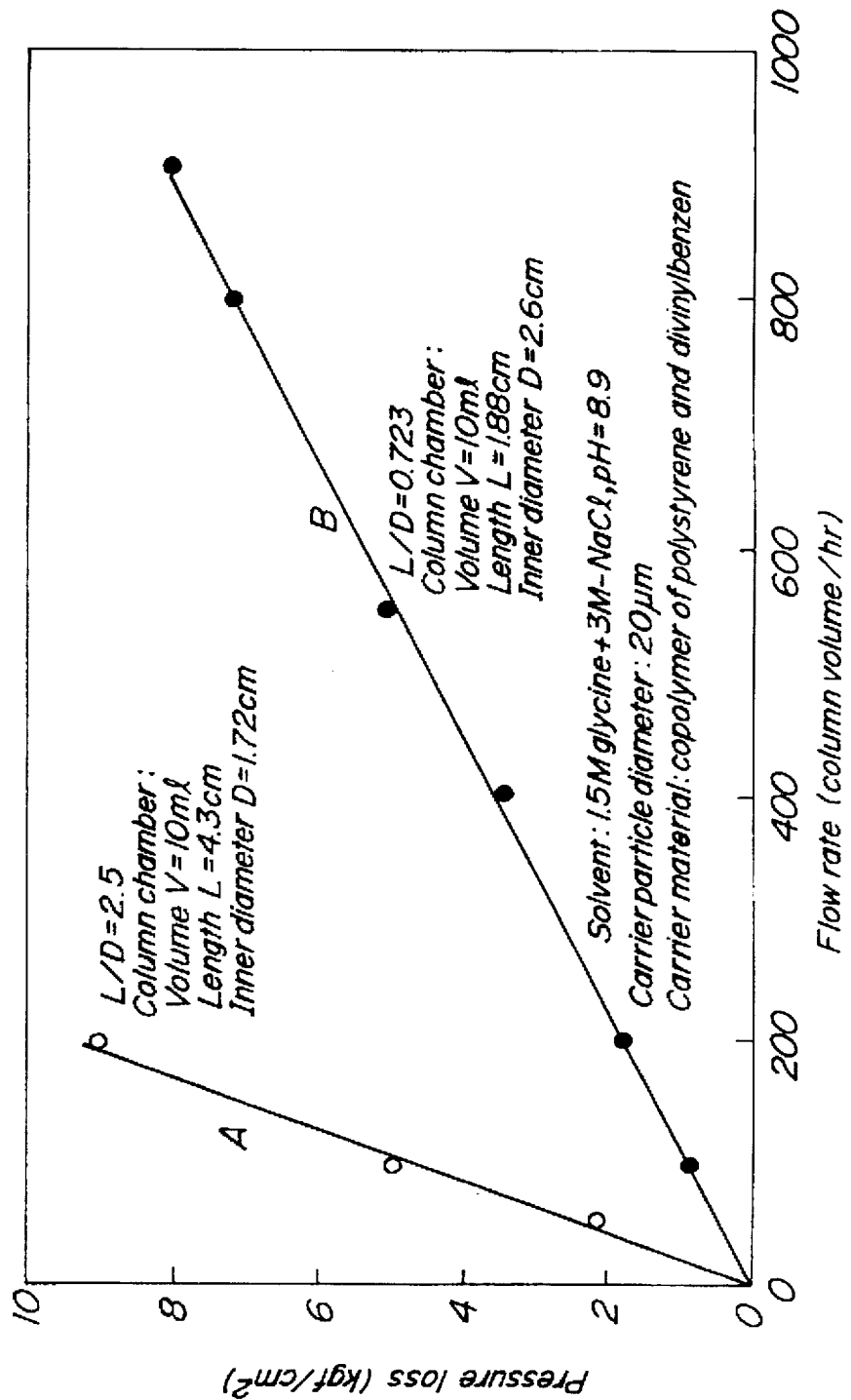
FIG. 12 is a diagram illustrating the pressure loss when a solvent (1.5M glycine+3M-NaCl, pH 8.9) was flown through a column at various flow rates.

As mentioned above, the investigation of the relationship between the flow rate and the pressure loss revealed that the separating and purifying operation is effected preferably at the pressure loss of not more than 7 kgf/cm$^2$ under the high flow rate of 200 column volume/hr when the ratio of the length/diameter of the column chamber is not more than 2. FIG. 12 shows the pressure loss when the solvent (1.5M glycine+3M-NaCl, pH 8.9) was passed through the column device at two flow rates. It is seen from FIG. 12 that in the case B in which the L/D is less than 2, the pressure loss was as low as not more than 2 kgf/cm$^2$ even under the flow rate of 200 column volume/hr, whereas in the case A with the L/D being more than 2, the pressure loss is more than 9 kgf/cm$^2$ when the flow rate was 200 column volume/hr.

According to the inventors' experiments, it was made clear that the column device according to the present invention is suitable for the separation and purification with a variety of the chromatography carriers having high performance charged therein. The inventors have investigated the relationship between the linear speed (flow rate) and the adsorbing capacity in the state that the chromatography carrier was charged into the column of the present invention, and discovered that the scaling up of the column device can be appropriately related to the staying time. The staying time is a time period from a point of time when the solvent is introduced into the column device or the column chamber to a point of time when the solvent is discharged from the column device or the column chamber. That is, the column device can be scaled up by increasing the volume of the column chamber with reference to a 10% breakthrough adsorbing capacity without being influenced by the linear speed (cm/hr), while the flow rate (column volume/hr) is being kept constant. According to the common indication of the flow rate by the linear flow rate, the flow rate (ml/hr) is varied by the diameter of the column chamber even if the volume inside the column is the same. Therefore, it is considered preferable to optimize the separating/purifying condition by the indication of the flow rate (column volume/hr, cv/hr) based on the staying time. Experiments: In the following, the present invention will be explained in more detail with reference to the following experiments.

Antibody Separating Test No. 1

Figure 13:
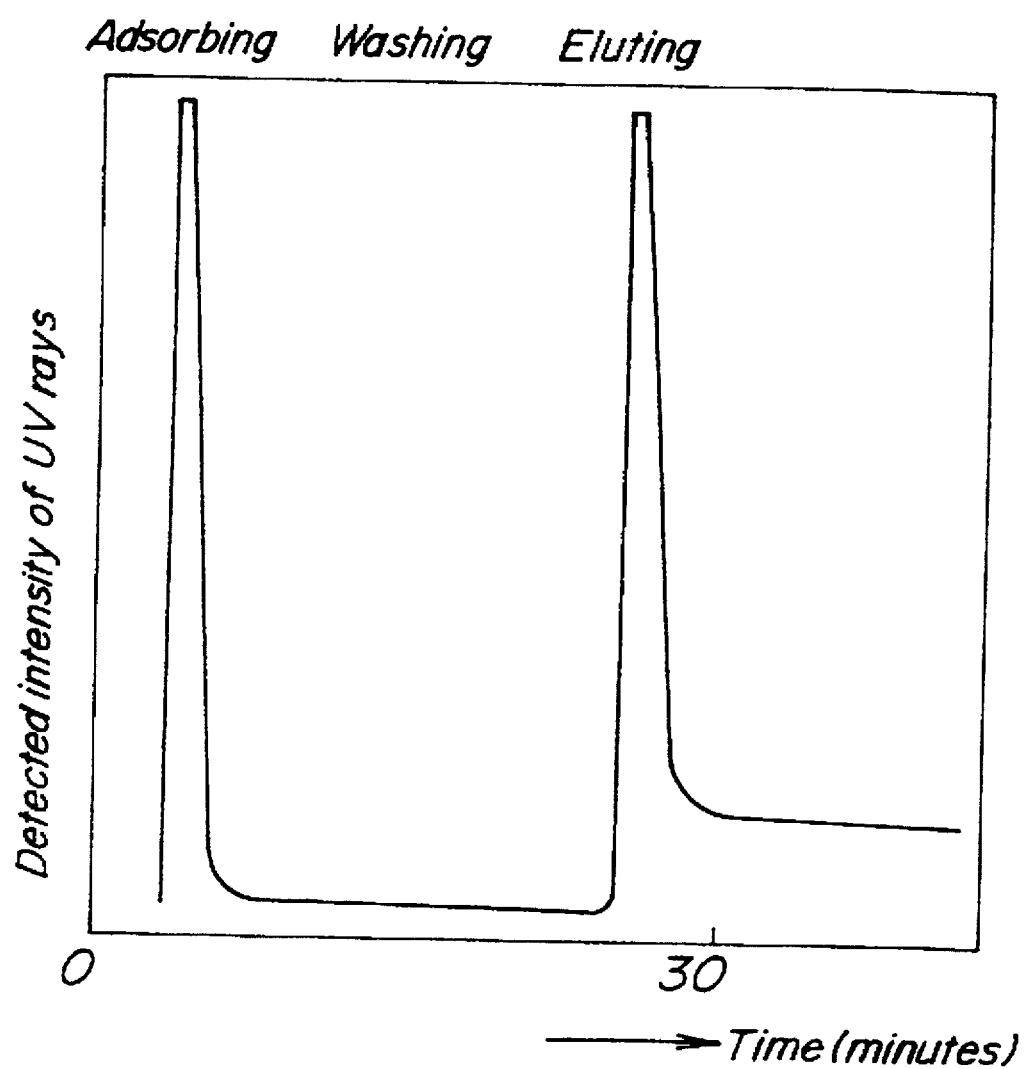
FIG. 13 is a diagram illustrating the relationship between the eluting time and the detected amount of ultraviolet rays with respect to Anti-body separating Test No. 1.

A column device for the low pressure-high speed liquid chromatography according to the present invention was set to the low pressure-high speed liquid chromatography system shown in FIG. 3. An antiserum, 250 μl, preliminarily filtered with a filter having pores of not more than 0.8 μm was passed through the column device at a treating flow rate of 80 column volume/hr (4 ml/min.), and adsorbed onto a filler. Thereafter, the column device was washed by passing a wash liquid (20 mM phosphate buffer, pH 7.4) through the column device for 12 minutes, and next the antibody (IgG) adsorbed onto the granular filler was eluted by passing an eluting liquid (0.1M citric acid+0.15M-NaCl, pH 4) through the column device for 10 minutes. Ingredients contained in the liquid eluted from the column were measured with the UV detector, thereby obtaining a chart in FIG. 13. It is seen from this chart that the antibody (IgG) was extremely excellently adsorbed and eluted. As the granular filler, a high speed type affinity chromatography carrier was charged, in a wetted state, into the column chamber. In the affinity chromatography carrier, silica gel having the average diameter of 30 μm was used as a base material, and Protein A was used as a ligand. The liquid was flown through the column device in the order of the inflow opening of the central portion of the head portion, the column chamber and the outflow opening in the cylindrical column body. A calibration test before passing the antiserum revealed that the pressure of 3 kgf/cm$^2$ was generated inside the column chamber in the case of 4 ml/min. (80 column volume/hr).

The maximum flow rate of the gear pump assembled into the chromatography system used was 50 ml/min., and the separating and purifying operation was effected at the treating flow rate of 80 column volume/hr. In that case, a column having a column volume up to 37.5 ml can be fitted to the system. An amount of the granular filler can be selectively determined, based on the adsorbing volume of the granular filler and the amount (treating amount) of the intended material contained in the liquid to be treated. In this test, the amount of the filler was about 1 ml. In order to set the purifying time period at 30 minutes, the column was used, in which the volume of the column chamber was set at 3 ml, and the ratio of the length/the diameter of the column chamber was 0.6. The outer diameter R1 of the cylindrical column body was 23 mm, the inner diameter R2 of the pressure-proof ring was 22.57 mm, the length L of the inserting portion of the head portion was 10 mm, and the diameters of the inflow opening and the outflow opening were 4 mm and 2 mm, respectively.

Antibody Separating Test 2

Figure 14:
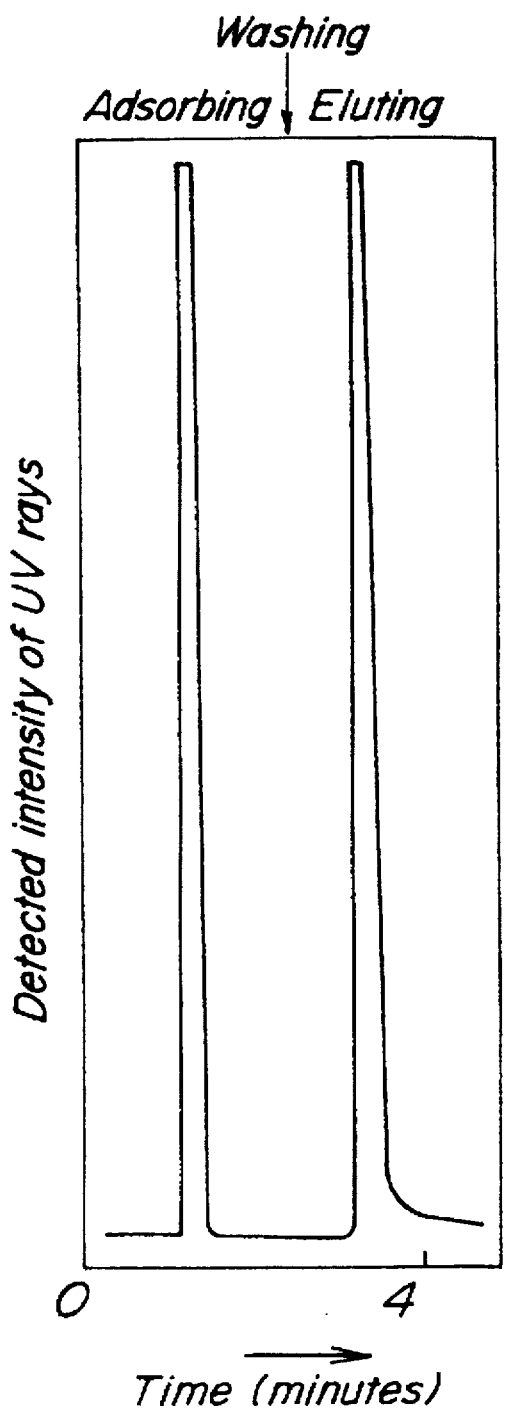
FIG. 14 is a diagram illustrating the relationship between the eluting time and the detected amount of ultraviolet rays with respect to Anti-body separating Test No. 2.

Into the same column as in Antibody Separating Test No. 1 was charged a perfusion type chromatography carrier or media, as a granular filler, made of a copolymer between styrene and divinylbenzene, and the column device was set to the low pressure-high speed liquid chromatography system shown in FIG. 3. An antiserum, 250 μl preliminarily filtered with a filter having pores of not more than 0.8 μm was passed through the column device at a treating flow rate of 10 ml/min. for 2 minutes, and adsorbed onto the filler. Therefore, the column device was washed by passing a wash liquid (20 mM phosphate buffer, pH 7.4) through the column device, and next the antibody IgG adsorbed onto the granular filler was eluted by passing an eluting liquid (0.1M citric acid +0.15M-NaCl, pH 4) through the column device for 2 minutes. Ingredients contained in the liquid eluted from the column were measured with the UV detector, thereby obtaining a chart in FIG. 14. It is seen from this chart that the antibody IgG was extremely excellently adsorbed and eluted. As shown in FIG. 8 in section, the perfusion type carrier had the average particle diameter of 20 μm, and was porous in that the carrier had a number of through holes and adsorbing pores. A calibration test before passing the antiserum revealed that the pressure of 0.7 kgf/cm$^2$ was generated inside the column chamber in the case of 10 ml/min. (200 column volume/hr).

Antibody Separating Test No. 3

The high speed affinity chromatography carrier using Protein A as a ligand was charged, as the granular filler, into the column in the same manner as in Antibody Separating Test No. 1, and the column device was set to the low pressure-high speed liquid chromatography system shown in FIG. 3. An antibody IgG was separated from a supernatant liquid in a serum-containing culture, 1.5 liters, preliminarily filtered with a filter having pores of not more than 0.45 μm. A column with a column space having a volume of 10 ml and a ratio of length/diameter of 0.81 was used. The outer diameter R1 of the cylindrical column body was 30 mm, the inner diameter R2 of the pressure-proof ring was 29.57 mm, the length L of the inserting portion of the head portion was 13 mm, and the diameters of the inflow opening and the outflow opening were 4 mm and 2 mm, respectively. The liquid was passed through the column device at 17 ml/min. under pressure of 2 kgf/cm$^2$. As is the same as in Antibody Separating Test Nos. 1 and 2, it was confirmed that the antibody IgG was extremely effectively separated and eluted in this test.

Separating Test Nos. 4 through 6

Figure 15:
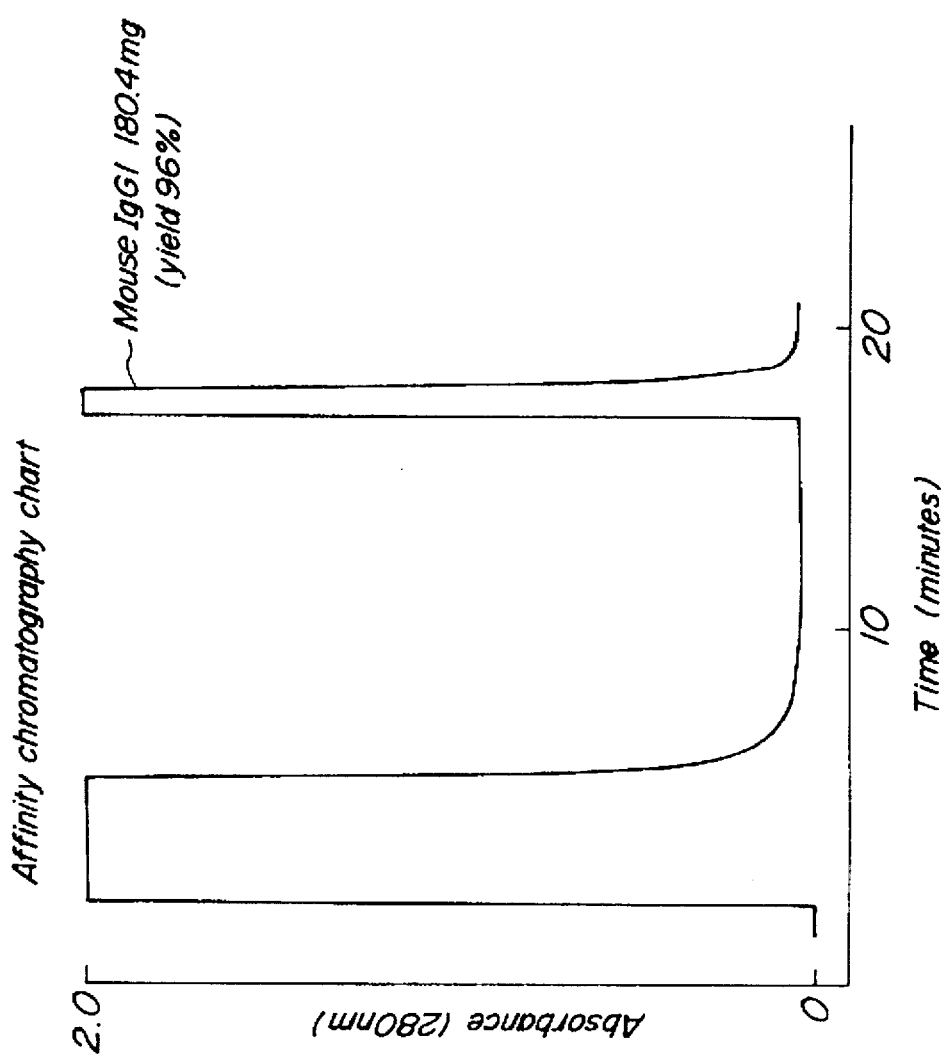
FIG. 15 is a diagram illustrating the relationship between the eluting time and the detected amount of ultraviolet rays when the affinity chromatography was effected, by using a column for low pressure-high speed liquid chromatography according to the present invention.
Figure 16:
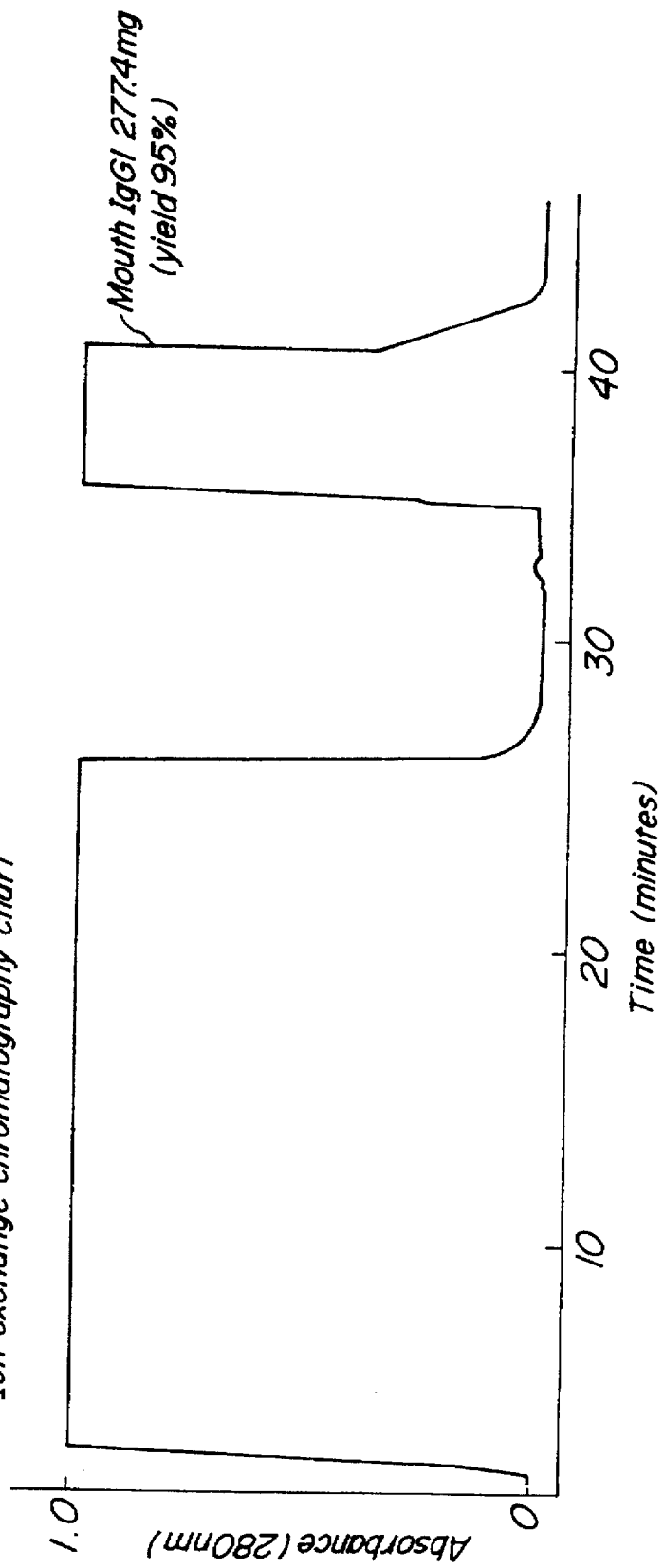
FIG. 16 is a diagram illustrating the relationship between the eluting time and the detected amount of ultraviolet rays when the supernatant liquid of a serum culture was separated and purified, by using the column for low pressure-high speed liquid chromatography according to the present invention.
Figure 17:
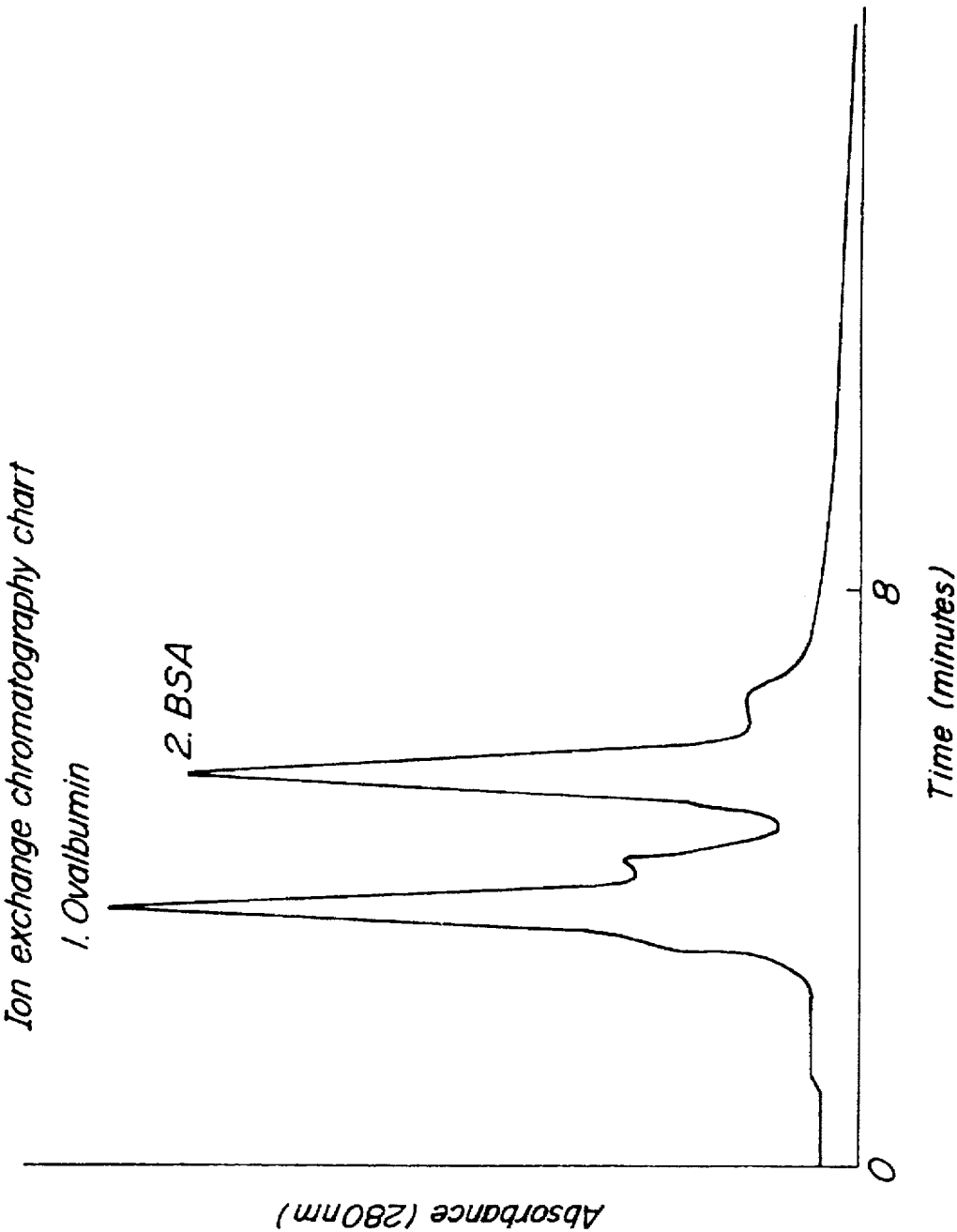
FIG. 17 is diagram illustrating the relationship between the eluting time and the detected amount of ultraviolet rays when ion exchange chromatography was effected by using the column for low pressure-high speed liquid chromatography according to the present invention.

Further Separation Tests were conducted. Results are shown in FIGS. 15–17, respectively.

Separating Test No. 4 (Affinity chromatography)

Sample: Mouse ascites (Mouse IgG1), 7.5 mg-IgG (25 ml)
Used column: column chamber volume 20 ml, column chamber length/diameter 1.46, Protein A plastic column (gel 20 ml, 26×38 mmL)
Flow rate: Adsorption ... 20 ml/min. (60 column volume/hr)
Washing ... 20 ml/min. (60 column volume/hr)×20 minutes
Eluting ... 10 ml/min. (30 column volume/hr)
Buffer: Adsorbing/washing liquid ... 1.5M glycine +3M-NaCl (pH 8.9) Eluting liquid ... phosphoric acid-citric acid rubber solution (pH 6)
Purifying time: 25 minutes
Yield: 96% (Mouse IgG 189.4 mg)

Separating Test No. 5 Process scale purification
Sample: Supernatant liquid in Serum culture (Mouse IgG1), 0.73 mg/ml (400 ml)
Used column: column chamber volume 50 ml, column chamber length/diameter 1.0, Protein A plastic column (gel 50 ml, 40×40 mmL)
Flow rate: Adsorption ... 50 ml/min. (60 column volume/hr)
Washing ... 50 ml/min. (60 column volume/hr)×10 minutes
Eluting ... 20 ml/min. (24 column volume/hr)
Buffer: Adsorbing/washing liquid ... 1.5M glycine +3M-NaCl (pH 8.9) Eluting liquid ... phosphoric acid citric acid rubber solution (pH 6)
Purifying time: 45 minutes
Yield: 95% (mouse IgG 277.4 mg)

Separating Test No. 6 (Ion Exchange Chromatography)
Sample: Mixture of ovalbumin and bovine albumin (Use amount of each of them: 1 mg)
Used column: column chamber volume 5 ml, column chamber length/diameter 0.8, Poros® 20 HQ (Strong anion exchanger), pressure loss 6 kgf/cm$^2$
Flow rate: Adsorption ... 10 ml/min. (120 column volume/hr)
Washing ... 10 ml/min. (120 column volume/hr)×2 minutes
Eluting ... 10 ml/min. (120 column volume/hr)
Buffer: Adsorbing/washing liquid ... 50 mM tris-HCl (pH 8.5) Eluting liquid ... 50 mM tris-HCl+0.5M Nacl (pH 8.5)
Purifying time: 8 minutes
Yield: 96% (ovalbumin), 95% (bovine albumin) (BSA)

What is claimed is:

1. A column for low pressure-high speed liquid chromatography, comprising:
a column body having an integral structure comprised of a transparent or translucent resin and including (i) a main body portion having first and second opposite ends, said first end being open, and (ii) a spout-like extension extending from the second end and forming an outflow opening;

a pair of upstream and downstream filters provided in said column body to form a column chamber therebetween, said column chamber receiving a granular chromatographic filler therein;

a head portion comprised of resin, said head portion being detachably secured to said first end of the column body having an inflow passageway extending therethrough, and including an insertion portion extending into an interior of the column body and a pressure-proof ring fitted around an outer periphery of the first end of the column body such that the pressure-proof ring opposes the insertion portion of the head portion that extends into the interior of the column body.

2. The column of claim 1, wherein said head portion is comprised of transparent or translucent resin, and each of said column body and said head portion is comprised of a material selected from the group consisting of polypropylene, high density polyethylene, polysulfone and polyvinyl chloride.

3. The column of claim 1, wherein an interior surface of the column body along the first end has a stepped structure, and an exterior surface of the insertion portion has a stepped structure for engaging the stepped structure of the column body.

4. The column of claim 3, wherein said head portion comprises a large diameter portion, and said insertion portion extends axially from the large diameter portion, said insertion portion being sealingly fitted into the first end of the column body.

5. The column of claim 4, wherein said insertion portion of the head portion has a cylindrical shape, and an outer peripheral surface of the insertion portion and an inner peripheral surface of the first end of the column body are threaded such that the insertion portion and the first end of the column body threading engage each other.

6. The column of claim 1, wherein said column chamber has a cylindrical shape, and a ratio of the axial length of the column chamber to a diameter of the column chamber is not greater than 2.

7. The column of claim 1, wherein said head portion comprises a large diameter portion, and said insertion portion extends axially from the large diameter portion, said insertion portion being sealingly fitted into the first end of the column body.

8. The column of claim 7, wherein said insertion portion of the head portion has a cylindrical shape, and an outer peripheral surface of the insertion portion and an inner peripheral surface of the first end of the column body are threaded such that the insertion portion and the first end of the column body threading engage each other.

9. The column of claim 1, further comprising an O-ring fitted within a circumferential groove provided in the head portion, said O-ring facing an end face of the first end of the column body to provide a seal between said end face and the head portion.

10. The column of claim 1, wherein a surface of the head portion that faces an interior of the column body has a concave contour.

11. A column for low pressure-high speed liquid chromatography, comprising:

a column body having an integral structure comprised of a transparent or translucent resin and including a main body portion having first and second opposite ends, said first end being open, and said second end being partially closed to form a small-diameter outflow opening;

a pair of upstream and downstream filters provided in said column body to form a column chamber therebetween, said column chamber receiving a granular chromatographic filler therein; and a head portion comprised of resin, said head portion being detachably secured to said first end of the column body and having an inflow passageway extending therethrough, and including an insertion portion extending into an interior of the column body; and a pressure-proof ring fitted around an outer periphery of the first end of the column body such that the pressure-proof ring opposes the insertion portion of the head portion that extends into the interior of the column body.

12. The column of claim 11, wherein said column chamber has a cylindrical shape and said outflow opening has a diameter substantially smaller than the diameter of the column chamber.

* * * * *